United States Patent [19]

Goolsby

[11] Patent Number: 4,489,277

[45] Date of Patent: Dec. 18, 1984

[54] CATHODIC PROTECTION MONITORING SYSTEM

[75] Inventor: Alvin D. Goolsby, Houston, Tex.

[73] Assignee: Shell Oil Company, Houston, Tex.

[21] Appl. No.: 336,666

[22] Filed: Jan. 4, 1982

[51] Int. Cl.³ ............................................. G01N 27/42
[52] U.S. Cl. .................... 324/425; 324/71.1; 204/196
[58] Field of Search ................ 324/425, 71.1, 65 CR, 324/71.2; 204/196, 197

[56] References Cited

U.S. PATENT DOCUMENTS

| 3,649,492 | 3/1972 | Marsh et al. | 324/71.2 |
| 3,657,084 | 4/1972 | Beer et al. | 204/197 |
| 4,089,767 | 5/1978 | Sabins | 204/197 |

FOREIGN PATENT DOCUMENTS

| 1430214 | 3/1976 | United Kingdom . |
| 2025056A | 1/1980 | United Kingdom . |
| 2057138A | 3/1981 | United Kingdom . |
| 1589244 | 5/1981 | United Kingdom . |

Primary Examiner—Michael J. Tokar
Assistant Examiner—Kevin D. O'Shea

[57] ABSTRACT

An apparatus for monitoring a cathodic protection system on a structure which is positioned in water such that a portion of the structure is beneath the surface of the water, such apparatus comprising: an insulating means positioned adjacent to the structure below the surface of the water; a metallic body positioned adjacent to the insulating means so that the body is electrically insulated from the structure; means for electrically connecting the body to the structure at a point above the surface of the water; and means for measuring the amount of current flowing through the electrical connecting means.

2 Claims, 2 Drawing Figures

CATHODIC PROTECTION MONITORING SYSTEM

BACKGROUND OF THE INVENTION

This invention relates generally to a method of monitoring the activity of a cathodic protection system installed on a metallic structure that is located underwater.

Cathodic protection is a method of combating corrosion of metals that are exposed to the action of water, such as in the case of offshore drilling and production platforms and pipelines. The purpose of cathodic protection is to reduce or eliminate oxygen-driven corrosion of steel or other metals in a given environment, such as seawater or saline mud. The corrosion of metal in an electrolyte at ambient temperature is an electrochemical process involving the flow of electrons in metals and ions in electrolytes. The corrosion can be controlled by the application of currents from an external source, for example, a generator or rectifier or from a galvanic sacrificial anode, which supplies all of the current for the electrochemical reduction of the corrodant oxygen by a source other than the corroding steel. If all of the current for the electrochemical reduction is supplied by the external source, the corrosion of the steel is stopped. The full protection of the structure is evidenced by the shift in potential of the steel from the initially freely-corroding potential of about $-500$ to $-600$ millivolts, versus a silver/silver chloride reference half cell, to values more negative than $-780$ millivolts when the cathodic protection is applied.

Generally, galvanic cathodic protection is obtained on offshore structures by the installation of large numbers of sacrificial aluminum alloy anodes to the structure. The average current density provided by the cathodic protection system is extremely important in providing full protection of the structure and in providing an indication of the life span of the galvanic anodes. Prior art workers have designed galvanic cathodic protection systems with a predetermined current density provided by a predetermined number of sacrificial anodes, each of which is a predetermined weight and size. However, since prior art workers have not had any means by which the actual cathodic current density provided by the protection system could be measured, these systems have generally been designed conservatively to ensure that the proper degree of protection is attained; this results in the installation of more anodes than are actually necessary to provide the proper degree of protection. These additional sacrificial anodes are costly and add to both the weight and the wave loading of the structure. Consequently, the structure must be designed to carry the additional weight of the unnecessary anodes and to withstand the greater wave loading caused by the anodes and the larger structure which results in a considerable and unnecessary expense in the construction of the structure.

Therefore, it is an object of the present invention to provide an apparatus for monitoring a cathodic protection system on an offshore structure to provide an indication of the current density provided by the cathodic protection system.

SUMMARY OF THE INVENTION

In accordance with the present invention there is provided an apparatus for monitoring a cathodic protection system on a structure which is positioned in water such that a portion of the structure is beneath the surface of the water, such apparatus comprising: an insulating means positioned adjacent to the structure below the surface of the water; a metallic body positioned adjacent to the insulating means so that the body is electrically insulated from the structure; means for electrically connecting the body to the structure at a point above the surface of the water; and means for measuring the amount of current flowing through the electrical connecting means.

In the preferred embodiment, the metallic body is a plate which is insulated from the structure by, for example, a layer of rubber which is sized to be slightly larger than the plate to ensure that the plate is electrically insulated from the structure. The layer of rubber and the metallic plate are wrapped around a member of the structure to conform essentially to the shape of the member. Preferably, a reference half cell is positioned near the plate so that the potential difference between the plate and the reference half cell can be determined. Accordingly, with the information provided by the present invention, it can be determined whether the cathodic protection system installed on the present structure can be reduced when installed on future structures to minimize the cost of both the cathodic protection system and the structure itself while ensuring that adequate protection is obtained. Moreover, the information provided by the present invention also makes it possible to calculate the life span of the cathodic protection system, thereby providing advance warning of any necessary maintenance.

Other objectives, advantages and applications of the present invention will be made apparent by the following detailed description of the preferred embodiments of the present invention.

DETAILED DESCRIPTION OF THE PREFERRED EMBODIMENTS

Figure 1:
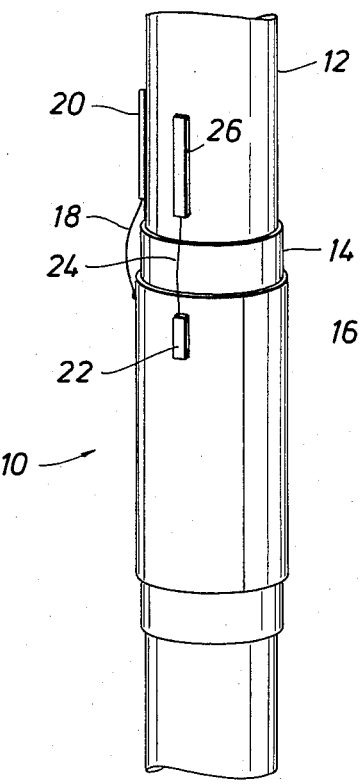
FIG. 1 is a sectional view in side elevation of an offshore structure utilizing the present invention.

Referring to FIG. 1, a monitoring section, which is indicated generally by numeral 10, is shown positioned on a circular member 12 of an offshore structure. Monitoring section 10 consists of an insulating layer 14, which is positioned around member 12, and a metallic plate 16 wrapped around insulating layer 14. Insulating layer 14 is sized so that it is longer than plate 16, and plate 16 is positioned so that a portion of insulating layer 14 extends beyond each end of plate 16 to ensure that plate 16 is electrically insulated from member 12. An insulated wire 18 is connected to plate 16 by welding or other suitable means and is passed through a conduit 20 to a point located above the surface of the water. A reference half cell 22 is positioned near plate 16; the output of half cell 22 is provided on wire 24 which is passed through conduit 26 to a point above the surface of the water.

Figure 2:
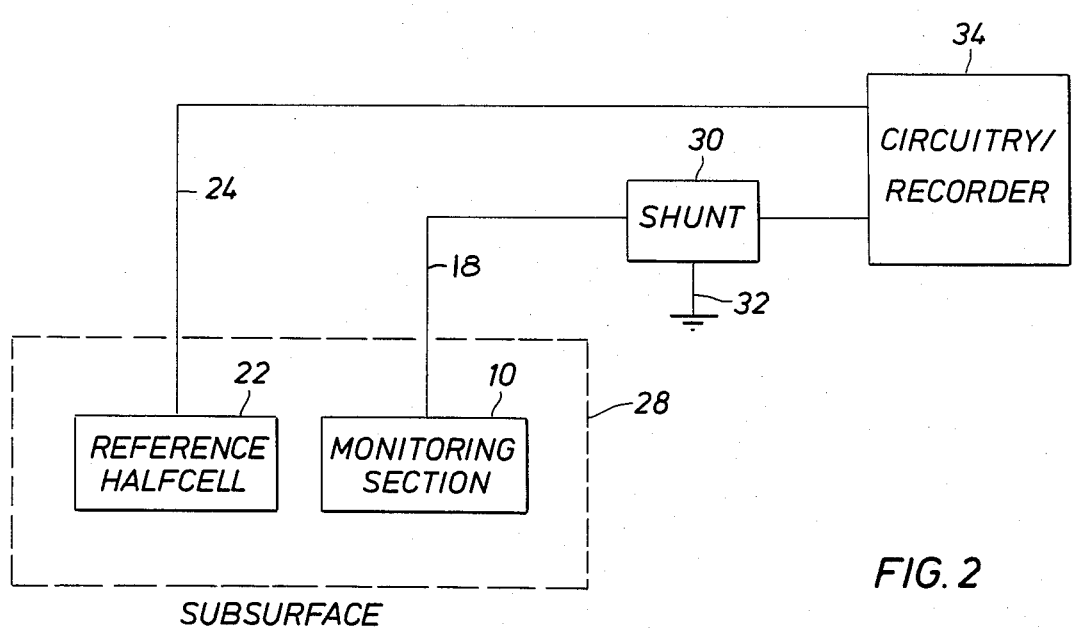
FIG. 2 is a schematic block diagram showing a cathodic protection monitoring system according to the present invention.

FIG. 2 illustrates a schematic block diagram of the cathodic protection monitoring system of the present invention. Monitoring section 10 and reference half cell 22 are indicated as being below the surface of the water by dotted lines 28. Monitoring section 10 is connected to shunt 30 by wire 18. Shunt 30 is connected to the structure as indicated by ground symbol 32, and it is also connected to circuitry/recorder 34. Reference half cell 22 is connected to circuitry/recorder 34 by wire 24. Circuitry/recorder 34 records the voltage difference between reference half cell 22 and monitoring section 10 and also the voltage across shunt 30, which is a function of the current flowing from monitoring section 10 through shunt 30 to point 32 of the structure and the predetermined resistance of shunt 30. Circuitry/recorder 34 may record the voltages continuously, or it may include a timer which enables the recording portion at predetermined intervals, such as each hour. If desired, the output from shunt 30 may be modified by circuitry/recorder 34 so that the signal recorded has the units amperes per square foot of monitoring section 10.

Two of the cathodic protection monitoring systems of the present invention were installed at 40 and 175 feet below the surface of the water on a platform located offshore of Southern California. These monitoring systems were tested on the platform from Jan. 6, 1980 to Jan. 6, 1981, with data being recorded every hour. The monitoring sections 16 which are described hereinbelow in detail performed satisfactorily during the test period. It should be noted that the following data concerning the specifics of the monitoring sections that were utilized in the test are provided for purposes of illustration and not limitation. Insulating layer 14 consisted of a piece of rubber which was 48 inches long and one-half inch thick and sized to fit around a circular member of the structure having a 14-inch diameter. Metallic plate 16 consisted of a steel plate which was 36 inches long and 3/16 inches thick and was sized to be wrapped around insulating layer 14. Plate 16 was positioned on insulating layer 14 so that approximately 6 inches of insulating layer 14 extended above and below plate 16. Wire 18 consisted of 4/0 insulated copper wire, and half cell 22 consisted of a silver/silver chloride reference half cell.

It is to be understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

What is claimed is:

1. An apparatus for monitoring a cathodic protection system on a structure which is positioned in water such that a portion of said structure is beneath the surface of said water, comprising: an insulating means positioned adjacent to said structure below the surface of said water; a metallic body positioned adjacent to said insulating means so that said body is electrically insulated from said structure; means for electrically connecting said body of said structure at a point above the surface of said water; means for measuring the amount of current flowing through said electrical connecting means; a half cell positioned near said body; means connected to said body and said half cell for measuring the voltage difference across said body and said half cell; and means connected to said current measuring means for determining the current density on said body.

2. An apparatus for monitoring a cathodic protection system on a structure which is positioned in water such that a portion of said structure is beneath the surface of said water, comprising: a rubber insulating means positioned adjacent to said structure below the surface of said water; a steel plate positioned adjacent to said insulating means so that said plate is electrically insulated from said structure; means for electrically connecting said plate to said structure at a point above the surface of said water; means for measuring the amount of current flowing through said electrical connecting means; a half cell positioned near said plate; means connected to said plate and said half cell for measuring the voltage difference across said plate and said half cell; and means connected to said current measuring means for determining the current density on said body.

* * * * *